US00PP14350P39

(12) United States Plant Patent

Zipperer, III

(10) Patent No.: US PP14,350 P3
(45) Date of Patent: Dec. 9, 2003

(54) GLADIOLUS PLANT NAMED 'GOLDEN GODDESS'

(50) Latin Name: *Gladiolus l.*
Varietal Denomination: Golden Goddess

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 41 days.

(21) Appl. No.: 09/877,574

(22) Filed: Jun. 8, 2001

(65) Prior Publication Data

US 2002/0002724 P1 Jan. 3, 2002

(30) Foreign Application Priority Data

Jun. 9, 2000 (EP) ..... 2000/0890

(51) Int. Cl.[7] ..... A01H 5/00
(52) U.S. Cl. ..... Plt./301
(58) Field of Search ..... Plt./301

(56) References Cited

PUBLICATIONS

UPOV–Rom, hit on gladiolus plant named 'Golden Goddess', GTI Jouve Retrieval software, Plant Variety Database, 2002/03.*

U.S. patent application Ser. No. 09/745,086, Zipperer, III, filed Dec. 20, 2000.

U.S. patent application Ser. No. 09/742,726, Zipperer, III, filed Dec. 20, 2000.

U.S. patent application Ser. No. 09/877,571, Zipperer, III, filed Jun. 8, 2001.

U.S. patent application Ser. No. 09/877,572, Zipperer, III, filed Jun. 8, 2001.

U.S. patent application Ser. No. 09/877,573, Zipperer, III, filed Jun. 8, 2001.

U.S. patent application Ser. No. 09/877,575, Zipperer, III, filed Jun. 8, 2001.

U.S. patent application Ser. No. 09/918,662, Zipperer, III, filed Jul. 31, 2001.

U.S. patent application Ser. No. 09/918,660, Zipperer, III, filed Jul. 31, 2001.

U.S. patent application Ser. No. 09/918,663, Zipperer, III, filed Jun. 31, 2001.

* cited by examiner

*Primary Examiner*—Bruce R. Campell
*Assistant Examiner*—Anne Marie Grünberg
(74) *Attorney, Agent, or Firm*—Hahn Loeser & Parks, LLP; Laura G. Barrow

(57) ABSTRACT

A new and distinct gladiolus variety, designated 'Golden Goddess', is shown and described. Compared to the 'Goldfield' variety, the 'Golden Goddess' variety can also maintain six flowers in open bloom simultaneously in a water after harvest. The claimed variety differs from 'Goldfield' in that the 'Goldfield' variety produces stems that are 10 cm shorter with one to two less florets per stem.

2 Drawing Sheets

The present invention comprises a new and distinct variety of a *Gladiolus l.* referred to by the variety name 'Golden Goddess.'

BRIEF DESCRIPTION OF THE PHOTOGRAPHS

ASEXUAL REPRODUCTION

The new variety was originated by the Applicant in a controlled proprietary breeding program in Ft. Myers, Fla. wherein selected gladiolus varieties were crossed. (The provisional breeder's designation "3–10" was used in a related application for a Community plant variety right filed earlier in the European Union Community Plant Variety Office). The female parent was a salmon pink gladiolus variety named 'Jennie Lee' an unpatented released variety (by Jennie Lee Zipperer) characterized in part by a long stem, long head, and high floret count (i.e. 18–20 florets). The male parent was an unpatented rich yellow gladiolus variety named 'Goldfield,' characterized in part by having a good stem length, 15–16 florets, and a susceptibility to diseases such as Fusarium, Curvalaria, and Botrytis. The seeds were planted in Ft. Myers, Fla., and the selection of 'Golden Goddess' variety was made in Spring 1988. Asexual reproduction of the 'Golden Goddess' variety was achieved by collecting cormels from the first corm and growing said cormels to maturity in Ft. Myers, Fla. All subsequent asexual reproductions of the 'Golden Goddess' variety remain true to the original variety type.

BOTANICAL DESCRIPTION

Figure 1:
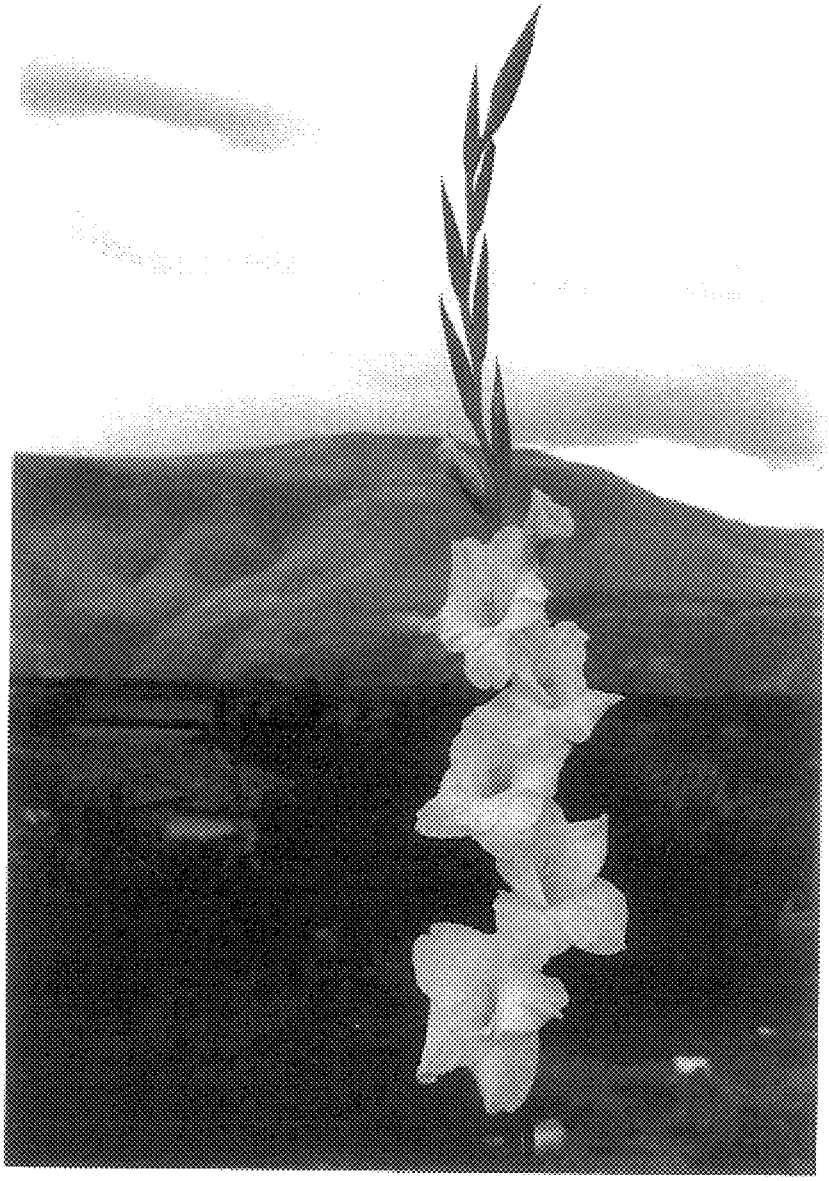
FIG. 1 is a photograph of a 'Golden Goddess' variety plant in bloom.

The accompanying color photograph (FIG. 1) shows the inflorescence and various stages of blooming of the 'Golden Goddess' variety plant. The plant was 98 days old when color of the flower was first seen (i.e. bloom tight condition), 100 days old when the bloom first opened (i.e. bloom perfect condition), and 103 days old when the bloom was declining (i.e. bloom going down).

The following botanical description, except for color, of the 'Golden Goddess' variety was observed when the plant was 98 days old grown under the following conditions in Ecuador:

1) Twelve-hour daylight days with high light intensity;

2) Temperatures: 58–60° F. (low's) and 69–75° F. (high's);

3) Humidity: 50–55%

4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

The spike of the plant is about 130 cm and comprises 16 florets when grown from #2 size corms (1.25 to 1.50 inches) in Ecuador. The color of the spike is Yellow Green 144C. The stem diameter below the first floret is about 1.2 cm. It should be noted, however, that various factors will affect spike length, including temperature (larger spikes occur in cooler weather and longer day lengths), irrigation, light intensity, fertilization, soil type (larger spikes occur in heavy soils versus sandy soil), and bulb size (larger bulbs result in larger spikes).

The leaf color of the 'Golden Goddess' variety is Green Group 137B. The leaf size is about 90 cm (length) by 3.5 cm (width).

Figure 2:
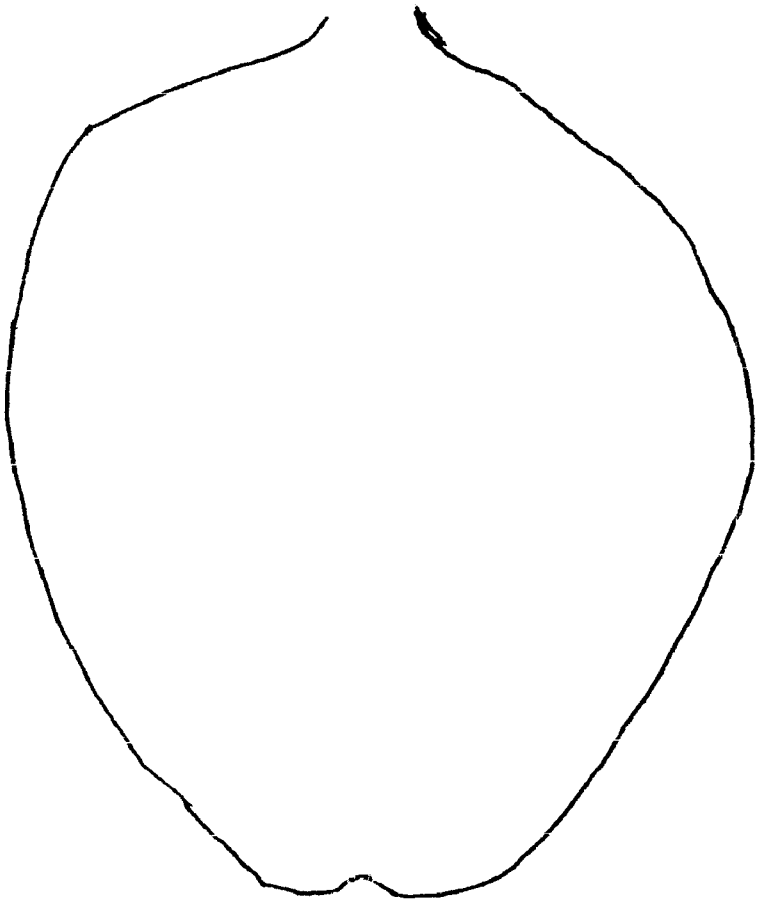
FIG. 2 is a drawing illustrating the shape and size of the petals.

The bud size of the 'Golden Goddess' variety is about 8 cm in length. The flowers of the variety each consist of a total of six petals of three different arrangements. In one arrangement, each bloom consists of two large petals oriented on the top part of the bloom, and two medium-size petals and two small-size petals oriented on the lower part of the bloom. In a second arrangement, the bloom consists of two large petals oriented on the top part of the bloom and three medium-sized petals and one small-sized petal oriented on the lower half of the bloom. Another arrangement consists of three large petals in the upper half of the bloom, two medium petals between 2:00 and 10:00 (referring to the face of a clock) on the lower half of the bloom, and one small petal positioned generally between 5:00 and 7:00 on the lower half of the bloom. FIG. 2 illustrates the shape and size of the large petals.

The diameter of the entire bloom is about 11 cm when grown from a #2 size corm in Ecuador. A stem cut with one bloom showing color takes two days for the first bloom to open completely. The bloom will hold open in perfect condition for 2.5 to 3 days. The spike will bloom for a period of eleven days.

The color of the corolla bloom tight is Yellow Group 2B. The color of the bloom in open perfect condition is Yellow Group 4B for the large and medium petals and Yellow Group 7D for the small petals. A small splash of Red Purple Group 64A can also be observed deep within the throat of the bloom. When the open flower starts to decline, the foregoing colors of the bloom remain the same.

The variety has three stamens and one pistil. The color of the pistil head and pistil stem is Green Yellow Group 1D. The color of the stamen head is Yellow White Group 158C. The color of the stamen stem is Green White Group 157D. With respect to the stamen, at the top of the stamen stem before the stamen head, the color changes to Red Purple 70B.

The corms of the 'Golden Goddess' variety are typical for the gladiolus and have a Greyed-Orange Group 170C color under the husk on the top of the bulb one day after harvest.

GENERAL OBSERVATIONS

The 'Golden Goddess' variety takes about 98 days to harvest, after planting, when grown from a #2 size corm in Ecuador. The variety can maintain six flowers in open bloom simultaneously in a vase of water after harvest from a stem just beginning to show color. This characteristic is similar to the variety's parent, 'Goldfield,' (also the most similar variety to 'Golden Goddess'), which requires 94 days to harvest after planting. The claimed variety differs from the 'Goldfield' variety in that the 'Goldfield' variety produces stems 10 cm shorter than 'Golden Goddess.' In addition, the 'Goldfield' variety produces one to two florets less than the claimed variety.

When compared to the 'Jennie Lee' parent variety, which harvests 84 days after planting, the 'Golden Goddess' variety is 14 days slower to harvest. The stem lengths are similar (i.e. about 130 cm when grown from a #2 size corm), but the 'Jennie Lee' variety produces one to two more florets per stem.

The 'Golden Goddess' variety has a good resistance to attack by Curvalaria fungi species but is similar to other yellow gladiolus varieties in that it is susceptible to Botrytis. The variety grows well throughout the entire year during both short and long day lengths. The variety also shows a good resistance to burning in hot weather.

The variety does not emit a fragrance.

I claim:

1. A new and distinct gladiolus variety of plant, 'Golden Goddess', as shown and described herein.

* * * * *